United States Patent
Seipel et al.

(10) Patent No.: US 6,207,140 B1
(45) Date of Patent: Mar. 27, 2001

(54) SUN SCREENING AGENTS IN THE FORM OF OIL/WATER MICRO EMULSIONS

(75) Inventors: Werner Seipel, Hilden; Bernd Fabry, Korschenbroich; Joerg Kahre, Leichlingen, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/254,946

(22) PCT Filed: Sep. 29, 1997

(86) PCT No.: PCT/EP97/05349

§ 371 Date: Mar. 19, 1999

§ 102(e) Date: Mar. 19, 1999

(87) PCT Pub. No.: WO98/15253

PCT Pub. Date: Apr. 16, 1998

(30) Foreign Application Priority Data

Oct. 7, 1996 (DE) .............................................. 196 41 274

(51) Int. Cl.$^7$ ............................... A61K 7/42; A61K 7/44; A61K 7/00
(52) U.S. Cl. .............................. 424/59; 424/60; 424/400; 424/401
(58) Field of Search ............................... 424/59, 60, 400, 424/401

(56) References Cited

U.S. PATENT DOCUMENTS

| | | |
|---|---|---|
| 1,985,424 | 12/1934 | Piggott . |
| 2,016,962 | 10/1935 | Flint et al. . |
| 2,703,798 | 3/1955 | Schwartz . |
| 4,172,887 | 10/1979 | Vanlerberghe et al. ................ 424/70 |
| 5,312,932 | 5/1994 | Behler et al. ............................ 554/90 |
| 5,322,957 | 6/1994 | Fabry et al. ............................. 558/23 |
| 5,374,716 | 12/1994 | Biermann et al. ................... 536/18.6 |
| 5,484,531 | 1/1996 | Kuehne et al. ....................... 210/651 |
| 5,576,425 | 11/1996 | Hill et al. ............................. 536/18.6 |
| 5,616,331 | 4/1997 | Allard et al. .......................... 424/401 |
| 5,730,993 | 3/1998 | Allard et al. .......................... 424/401 |
| 5,756,110 | 5/1998 | Allard et al. ............................ 424/40 |

FOREIGN PATENT DOCUMENTS

| | | |
|---|---|---|
| 1 165 574 | 3/1964 | (DE) . |
| 20 24 051 | 12/1971 | (DE) . |
| 42 04 700 | 8/1993 | (DE) . |
| 295 20 749 U | 4/1996 | (DE) . |
| 0 301 298 | 2/1989 | (EP) . |
| 0 561 825 | 9/1993 | (EP) . |
| 0 561 999 | 9/1993 | (EP) . |
| 0 667 144 | 8/1995 | (EP) . |
| 2252840 | 12/1978 | (FR) . |
| 962919 | 8/1961 | (GB) . |
| 1 333 475 | 10/1973 | (GB) . |
| WO90/03977 | 4/1990 | (WO) . |
| WO92/06984 | 4/1992 | (WO) . |
| WO94/05680 | 3/1994 | (WO) . |
| WO96/28131 | 9/1996 | (WO) . |

OTHER PUBLICATIONS

P. Finkel, *Sonnenschutzmittel—Wirkstoffe und Formulierungen* Parf.Kosm. vol. 76, (1995) pp. (432–435).
S. Schauder, *Trends beim Sonnenschutz*, Parf. Kosm. vol. 76, (1995) pp. 490–491).
A. Biswas and B. Mukherji, Surface–Active Properties of Sodium Salts of Sulfated Fattty Acid Monoglycerides, J. Am. Oil. Chem. Soc. vol. 37, (1960) pp. (171–175).
F. Ahmed, Efficient Synthesis of Fatty Monoglyceride Sulfates from Fatty Acids and Fatty Acid Methyl Esters, J. Am. Oil. Chem. Soc. vol. 67, (1990) pp. (8–14).
M. Heike Kelkenberg, *Detergenzien auf Zuckerbasis*,Tenside Surfactants Detergents vol. 25, (1988) pp. (8–13).
K. Stanzl, J. Roding, L. Zastrow, *Die Entwicklung eines neuen Lichtschutzmittels*, Parf. Kosm. vol. 74 (1993) pp. (485–488).
"Kosmetische Farbemittel" (1984) pp. (81–106).

*Primary Examiner*—Shelley A. Dodson
(74) *Attorney, Agent, or Firm*—John E. Drach; Steven J. Trzaska

(57) ABSTRACT

A sun protection composition, in an oil-in-water microemulsion form, containing: (a) an oil component; (b) a monoglyceride (ether) sulfate; and (c) at least one ultraviolet filter.

20 Claims, No Drawings

SUN SCREENING AGENTS IN THE FORM OF OIL/WATER MICRO EMULSIONS

This application is a 371 of PCT/EP97 05349 filed Sep. 29, 1997

BACKGROUND OF THE INVENTION

This invention relates to sun protection compositions in the form of o/w microemulsions containing oils, selected anionic emulsifiers and UV filters and to the use of these mixtures for the production of sun protection compositions.

PRIOR ART

Under the influence of solar radiation, the pigmenting of normal skin leads to the formation of melanins. Exposure to long-wave UV-A light results in darkening of the melanins present in the epidermis without any harmful effects while exposure to short-wave UV-B radiation results in the formation of new melanin. However, before the protective pigment can be formed, the skin is exposed to the effect of unfiltered radiation which can lead to reddening of the skin (erythema), inflammation of the skin (sunburn) or even to blisters, depending on the exposure time. The strain on the organism associated with such skin lesions, for example in connection with the distribution of histamines, can additionally lead to headache, lassitude, fever, heart and circulation problems and the like. The consumer seeking to protect himself/herself against the harmful effects of the sun can choose from a range of products which, for the most part, are oils and milky emulsions which, besides a few skin-care ingredients, contain above all UV filters. Overviews on this subject have been published, for example, by P. Finkel in Parf. Kosm. 76, 432 (1995) and by S. Schauder in Parf. Kosm. 76, 490 (1995).

Nevertheless, there is a continuing need on the market for products with an improved performance spectrum. Of particular interest in this regard are compositions which enable relatively large amounts of UV filters to be incorporated without any phase separation or sedimentation occurring during storage. Where relatively large quantities of titanium dioxide are incorporated, a formulation produced by the phase inversion temperature method, as described for example in European patent application EP-A1 0 667 144 (L'Oreal), tends to separate the dispersed solid very quickly. Another problem is that many UV filters are capable of interacting with the other ingredients of the formulation, resulting in a chemical reaction and also in a reduction in storage stability. Finally, consumers prefer transparent formulations which show high skin-cosmetic compatibility, even when applied to very sensitive skin. Accordingly, the complex problem addressed by the present invention was to provide sun protection compositions which would be distinguished at one and the same time by particular phase stability, stability in storage, transparency and compatibility with sensitive skin.

DESCRIPTION OF THE INVENTION

The present invention relates to sun protection compositions in the form of o/w microemulsions containing (a) oils, (b) monoglyceride (ether) sulfates and (c) UV filters.

It has surprisingly been found that o/w microemulsions of the described type are extremely stable in storage, even where relatively large quantities of UV filters are incorporated, and are distinguished by particularly high skin-cosmetic compatibility. In addition, their particle fineness makes them transparent which contributes towards the aesthetic appearance of the products. The invention includes the observation that particularly advantageous compositions can be obtained by using mixtures of (b1) monoglyceride sulfates and (b2) alkyl ether sulfates, alkyl oligoglucosides and/or fatty acid-N-alkyl glucamides in a ratio by weight of 10:90 to 90:10 and preferably 25:75 to 75:25 as emulsifiers.

Oils

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer triol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons. Other suitable oils are silicone compounds, for example dimethyl polysiloxanes, methylphenyl polysiloxanes, cyclic silicones and amino-, fatty-acid-, alcohol-, polyether-, epoxy-, fluorine- and/or alkyl-modified silicone compounds which may be both liquid and resin-like at room temperature. The oils may be present in the compositions according to the invention in quantities of 1 to 90% by weight, preferably 5 to 75% by weight and more preferably 10 to 50% by weight, based on the non-aqueous component.

Monoglyceride (ether) Sulfates

Monoglyceride sulfates and monoglyceride ether sulfates are known anionic surfactants which may be obtained by the relevant methods of preparative organic chemistry. They are normally produced from triglycerides which are transesterified to the monoglycerides, optionally after ethoxylation, and then sulfated and neutralized. The partial glycerides may also be reacted with suitable sulfating agents, preferably gaseous sulfur trioxide or chlorosulfonic acid [cf. EP-B1 0561825, EP-B1 0561999 (Henkel)]. If desired, the neutralized products may be subjected to ultrafiltration to reduce the electrolyte content to the required level [DE-A1 4204700 (Henkel)]. Overviews of the chemistry of monoglyceride sulfates have been published, for example, by A. K. Biswas et al. in J. Am. Oil. Chem. Soc. 37, 171 (1960) and by F. U. Ahmed in J. Am. Oil. Chem. Soc. 67, 8 (1990).

The monoglyceride (ether) sulfates to be used in accordance with the present invention correspond to formula (I):

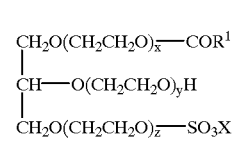

(I)

in which $R^1CO$ is a linear or branched acyl group containing 6 to 22 carbon atoms, x, y and z together stand for 0 or for numbers of 1 to 30, preferably 2 to 10, and X is an alkali metal or alkaline earth metal. Typical examples of monoglyceride (ether) sulfates suitable for the purposes of the invention are the reaction products of lauric acid monoglyceride, cocofatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of their sodium salts. Monoglyceride sulfates corresponding to formula (I), in which R¹CO is a linear acyl group containing 8 to 18 carbon atoms, are preferably used. The percentage content of monoglyceride (ether) sulfates is normally from 10 to 90% by weight, preferably from 25 to 75% by weight and more preferably from 40 to 60% by weight, based on the non-aqueous component.

Alkyl Ether Sulfates

Alkyl ether sulfates ("ether sulfates") which may be used as anionic co-emulsifiers are known surfactants which, on an industrial scale, are produced by $SO_3$ or chlorosulfonic acid (CSA) sulfation of fatty alcohol or oxoalcohol polyglycol ethers and subsequent neutralization. Ether sulfates suitable for use in accordance with the invention correspond to formula (II):

$$R^2O\text{---}(CH_2CH_2O)_mSO_3X \qquad (II)$$

in which $R^2$ is a linear or branched alkyl and/or alkenyl radical containing 6 to 22 carbon atoms, n is a number of 1 to 10 and X is an alkali metal and/or alkaline earth metal, ammonium, alkylammonium, alkanolammonium or glucammonium. Typical examples are the sulfates of addition products of on average 1 to 10 and more particularly 2 to 5 moles of ethylene oxide onto caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof in the form of their sodium and/or magnesium salts. The ether sulfates may have both a conventional homolog distribution and a narrow homolog distribution. It is particularly preferred to use ether sulfates based on adducts of on average 2 to 3 moles of ethylene oxide with technical $C_{12/14}$ or $C_{12/18}$ cocofattyl alcohol fractions in the form of their sodium and/or magnesium salts.

Alkyl and/or Alkenyl Oligoglycosides

Alkyl and alkenyl oligoglycosides are known nonionic surfactants corresponding to formula (III):

$$R^3O\text{---}[G]_p \qquad (III)$$

in which $R^3$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (III) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^3$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^3$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ cocoalcohol with a DP of 1 to 3 are preferred.

Fatty Acid N-alkyl Polyhydroxyalkylamides

Fatty acid N-alkyl polyhydroxyalkylamides which may also be usd as nonionic co-emulsifiers are nonionic surfactants which correspond to formula (IV):

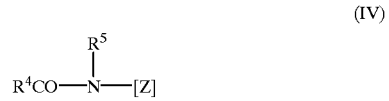

where $R^4CO$ is an aliphatic acyl radical containing 6 to 22 carbon atoms, $R^5$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups. The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (V):

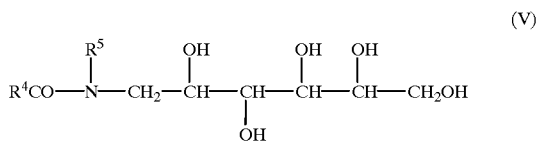

Preferred fatty acid N-alkyl polyhydroxyalkylamides are glucamides corresponding to formula (V) in which $R^5$ is an alkyl group and $R^4CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (V) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

The total percentage content of the co-emulsifiers mentioned—based on the non-aqueous component—is normally from 5 to 75% by weight, preferably from 10 to 50% by weight and more preferably from 15 to 30% by weight.

UV Filters

UV filters are organic substances which are capable of absorbing ultraviolet radiation and of releasing the energy absorbed in the form of longer wave radiation, for example heat. An overview of UV filters can be found, for example, in Parf. Kosm. 74, 485 (1993). Typical examples are 4-aminobenzoic acid and esters and derivatives thereof (for example 2-ethylhexyl-p-dimethyl aminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy-4-methoxybenzophenone), dibenzoyl methanes, salicylate esters, 2-phenylbenzimidazole-5-sulfonic acid, (1-(4-tert.butylphenyl)-3-(4'-methoxyphenyl)-propane-1,3-dione, 3-(4'-methyl)-benzylidene bornan-2-one, methyl benzylidene camphor and the like.

The compositions according to the invention may also contain finely dispersed metal oxides or salts as light filters. Typical examples are titanium dioxide, zinc oxide, iron oxide, aluminium oxide, cerium oxide, zirconium oxide, silicates (talcum) and barium sulfate. The particles should have a mean diameter of less than 100 nm, preferably between 5 and 50 nm and more preferably between 15 and 30 nm. They may be spherical in shape although particles ellipsoidal or otherwise non-spherical in shape may also be used.

Besides the two above-mentioned groups of primary light filters, the compositions according to the invention may also contain secondary light filters of the antioxidant type which interrupt the photochemical reaction chain initiated when UV radiation penetrates into the skin. Typical examples of these secondary light filters are Superoxid-Dismutase, tocopherols (vitamin E) and ascorbic acid (vitamin C).

The percentage content of UV filters in the compositions according to the invention, based on their non-aqueous component, is normally from 10 to 90% by weight, preferably from 25 to 75% by weight and more preferably from 40 to 60% by weight. The compositions to the invention as such may contain from 1 to 95% by weight, preferably from 5 to 80% by weight and more preferably from 10 to 60% by weight of water. If organic compounds are used as UV filters, the co-emulsifying properties of the formulations may be utilized for their production.

Microemulsions

Microemulsions are optically isotropic, thermodynamically stable systems which contain oil components, emulsifiers and water. The clear or rather transparent appearance of microemulsions is attributable to the small particle size of the dispersed emulsion droplets which is essentially below 300 nm and preferably in the range from 50 to 300 nm. In the range from 100 to 300 nm, the microemulsions obtained are brown-red in transmitted light and a shimmering blue in reflected light. Below a droplet diameter of 100 nm, microemulsions are clear. The microemulsions are preferably produced by a so-called cold process in which oils and emulsifiers are emulsified with water and the UV filters and optionally other additives are subsequently added. The required active substance content can be adjusted by addition of water and/or hydrotropes.

Commercial Applications

The compositions according to the invention are distinguished by high transparency and stability and by particularly advantageous skin-cosmetic compatibility. Typical preparations have the following composition:

(a) 1 to 90, preferably 5 to 80% by weight of oils, (b) 10 to 90, preferably 25 to 75% by weight of emulsifiers and (c) 10 to 90, preferably 25 to 75% by weight of UV filters, with the proviso that the quantities shown add up to 100% by weight. Within the concentration ranges mentioned, particularly stable fine-droplet microemulsions are obtained.

The compositions according to the invention may additionally contain small quantities of other anionic surfactants compatible with the other ingredients. Typical examples are soaps, alkyl benzenesulfonates, alkane sulfonates, olefin sulfonates, alkyl ether sulfonates, glycerol ether sulfonates, α-methyl ester sulfonates, sulfofatty acids, alkyl sulfates, glycerol ether sulfates, hydroxy mixed ether sulfates, fatty acid amide (ether) sulfates, mono- and dialkyl sulfosuccinates, mono- and dialkyl sulfosuccinimates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether)phosphates. Where polyglycol ether chains are present in the anionic surfactants, they may have a conventional homolog distribution, although the preferably have a narrow homolog distribution.

The compositions according to the invention may contain co-emulsifiers, superfatting agents, stabilizers, waxes, consistency promoters, thickeners, cationic polymers, biogenic agents, preservatives, hydrotropes, solubilizers, dyes and fragrances.

Suitable co-emulsifiers are, for example, nonionic surfactants from at least one of the following groups:

(b1) products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group;

(b2) $C_{12/18}$ fatty acid monoesters and diesters of products of the addition of 1 to 30 moles of ethylene oxide to glycerol;

(b3) glycerol monoesters and diesters and sorbitan monoesters and diesters of saturated and unsaturated fatty acids containing 6 to 22 carbon atoms and ethylene oxide adducts thereof;

(b4) adducts of 15 to 60 moles of ethylene oxide with castor oil and/or hydrogenated castor oil;

(b5) polyol esters and, in particular, polyglycerol esters such as, for example, polyglycerol polyricinoleate or polyglycerol poly-12-hydroxystearate. Mixtures of compounds from several of these classes are also suitable;

(b6) products of the addition of 2 to 15 moles of ethylene oxide to castor oil and/or hydrogenated castor oil;

(b7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b8) trialkyl phosphates;

(b9) wool wax alcohols;

(b10) polysiloxane/polyalkyl polyether copolymers and corresponding derivatives;

(b11) mixed esters of pentaerythritol, fatty acids, citric acid and fatty alcohol according to DE-PS 11 65 574 and (b12) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

Zwitterionic surfactants may also be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N—coco—alkylaminopropionate, cocoacylaminoethyl aminopropionate and $C_{12/18}$ acyl sarcosine. Besides the ampholytic emulsifiers, quaternary emulsifiers may also be used, those of the esterquat type, preferably methyl-quaternized difatty acid triethanolamine ester salts, being particularly preferred.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency promoters are, above all, fatty alcohols containing 12 to 22 and preferably 16 to 18 carbon atoms and, in addition, partial glycerides. These substances are preferably used in combination with alkyl oligoglucosides and/or fatty acid-N-methyl glucamides of the same chain length and/or polyglycerol poly-12-hydroxystearates. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols such as, for example, pentaerythritol or trimethylolpropane, narrow-range fatty alcohol ethoxylates or alkyl oligoglucosides and electrolytes such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lamequat®L Grünau), quaternized wheat polypeptides, polyethyleneimine, cationic silicone polymers such as, for example, Amidomethicone or Dow Corning (Dow Corning Co., USA), copolymers of adipic acid and dimethyl aminohydroxypropyl diethylenetriamine (Cartaretine®, Sandoz, CH), polyaminopolyamides as described, for example, in FR-A 2252840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearate. Biogenic agents in the context of the invention are, for example, bisabolol, allantoin, phytantriol, panthenol, AHA acids, plant extracts and vitamin complexes. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanediol or sorbic acid. Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. Finally, the invention relates to the use of the o/w microemulsions according to the invention for the production of sun protection compositions.

EXAMPLES

O/W microemulsions R1 to R6 according to the invention were produced by a cold process. To this end, the oils were emulsified in water together with the oil-soluble or oil-dispersible UV filters and the emulsifiers. Wax-like components were melted and incorporated at slightly elevated temperature while water-soluble or water-dispersible UV filters were introduced together with the aqueous phase. Water-clear microemulsions were obtained. The transmission of the emulsions was photometrically determined at 650 nm. Stability was evaluated after storage for 12 weeks at 40° C. The symbol (+++) signifies no phase separation/sedimentation while the symbol (++) signifies no phase separation/slight clouding. The results are set out in Table 1 below.

wherein $R^1CO$ is a linear or branched acyl group containing from 6 to 22 carbon atoms, x, y and z represent either 0 or a number from 1 to 30 and X is an alkali metal or alkaline earth metal.

4. The composition of claim 1 wherein the monoglyceride (ether) sulfate is present in the composition in an amount of from 10 to 90% by weight, based on the weight of the composition.

5. The composition of claim 1 wherein the ultraviolet filter is present in the composition in an amount of from 10 to 90% by weight, based on the weight of the composition.

6. The composition of claim 1 wherein the composition further comprises an emulsifier selected from the group consisting of an alkyl ether sulfate, an alkyl and/or alkenyl oligoglycoside, a fatty acid N-alkyl polyhydroxyalkylamide, and mixtures thereof.

7. The composition of claim 6 wherein the emulsifier is present in the composition in an amount of from 5 to 75% by weight, based on the weight of the composition.

8. The composition of claim 1 wherein the composition further comprises from 1 to 95% by weight, based on the weight of the composition, of water.

TABLE 1

O/W Microemulsions

| Component | INCI Name | R1 | R2 | R3 | R4 | R5 | R6 |
|---|---|---|---|---|---|---|---|
| Plantapon CMGS | Sodium Coco Monoglycerol Sulfate | 12.0 | 6.0 | 6.0 | 6.0 | 6.0 | 3.0 |
| Texapon N 70 | Sodium Laureth Sulfate | — | 6.0 | — | 3.0 | 2.0 | 4.0 |
| Plantacare ® 1200 | Dodecyl Polyglucose | — | — | 6.0 | 3.0 | 4.0 | 5.0 |
| Monomuls ® 90-O 18 | Glyceryl Oleate | 6.0 | — | — | — | — | — |
| Eutanol ® G | Octyldodecanol | 3.0 | 15.0 | — | — | — | 15.0 |
| Cetiol ® OE | Dicaprilyl Ether | — | 15.0 | — | — | — | 20.0 |
| Cetiol ® V | Decyl Oleate | — | — | 35.0 | — | — | — |
| Myritol ® 318 | Caprylic/Capric Triglyceride | — | — | — | 35.0 | — | — |
| Cetiol ® SN | Cetearyl Isononanoate | — | — | — | — | 35.0 | — |
| Parsol ® MCX | Methoxycinnamic acid-2-ethylhexyl ester | 5.0 | 9.0 | — | — | — | — |
|  | Methyl benzylidene camphor | — | — | 5.0 | — | — | — |
| Uvinul ® T 150 | Octyl Triazone | — | — | — | 5.0 | — | — |
| Titanium dioxide |  | — | — | — | — | 5.0 | — |
| Copherol ® F 1300 | Tocopherol | — | — | — | — | — | 10.0 |
| Water |  |  |  | ad 100 |  |  |  |
| Stability in storage |  | ++ | ++ | ++ | ++ | +++ | +++ |
| Transmission [%] |  | 92 | 90 | 90 | 92 | 95 | 95 |

What is claimed is:

1. A sun protection composition, in an oil-in-water microemulsion form, comprising:

(a) an oil component;

(b) a monoglyceride (ether) sulfate; and (c) at least one ultraviolet filter.

2. The composition of claim 1 wherein the oil component is present in the composition in an amount of from 1 to 90% by weight, based on the weight of the composition.

3. The composition of claim 1 wherein the monoglyceride (ether) sulfate corresponds to formula (I):

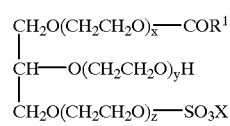

(I)

9. The composition of claim 1 wherein the composition further comprises an auxiliary component selected from the group consisting of a co-emulsifier, a superfatting agent, a stabilizer, a wax, a consistency promoter, a thickener, a cationic polymer, a biogenic agent, a preservative, a hydrotrope, a solubilizer, a dye, a fragrance, and mixtures thereof.

10. The composition of claim 9 wherein the auxiliary component is present in the composition in an amount of from 1 to 50% by weight, based on the weight of the composition.

11. A process for making a sun protection composition, in an oil-in-water microemulsion form, comprising:

(a) providing an oil component;

(b) providing a monoglyceride (ether) sulfate;

(c) providing at least one ultraviolet filter; and (d) mixing (a)–(c) to form the sun protection composition.

12. The process of claim 11 wherein the oil component is present in the composition in an amount of from 1 to 90% by weight, based on the weight of the composition.

13. The process of claim 11 wherein the monoglyceride (ether) sulfate corresponds to formula (I):

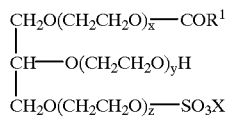

(I)

wherein $R^1CO$ is a linear or branched acyl group containing from 6 to 22 carbon atoms, x, y and z represent either 0 or a number from 1 to 30 and X is an alkali metal or alkaline earth metal.

14. The process of claim 11 wherein the monoglyceride (ether) sulfate is present in the composition in an amount of from 10 to 90% by weight, based on the weight of the composition.

15. The process of claim 11 wherein the ultraviolet filter is present in the composition in an amount of from 10 to 90% by weight, based on the weight of the composition.

16. The process of claim 11 further comprising adding to the composition an emulsifier selected from the group consisting of an alkyl ether sulfate, an alkyl and/or alkenyl oligoglycoside, a fatty acid N-alkyl polyhydroxyalkylamide, and mixtures thereof.

17. The process of claim 16 wherein the emulsifier is added to the composition in an amount of from 5 to 75% by weight, based on the weight of the composition.

18. The process of claim 11 further comprising adding water to the composition in an amount of from 1 to 95% by weight, based on the weight of the composition, of water.

19. The process of claim 11 further comprising adding to the composition an auxiliary component selected from the group consisting of a co-emulsifier, a superfatting agent, a stabilizer, a wax, a consistency promoter, a thickener, a cationic polymer, a biogenic agent, a preservative, a hydrotrope, a solubilizer, a dye, a fragrance, and mixtures thereof.

20. The process of claim 19 wherein the auxiliary component is added to the composition in an amount of from 1 to 50% by weight, based on the weight of the composition.

* * * * *